(12) United States Patent
Benaglia et al.

(10) Patent No.: US 9,284,258 B2
(45) Date of Patent: Mar. 15, 2016

(54) PROCESS FOR THE REDUCTION OF NITRO DERIVATIVES TO AMINES

(71) Applicant: Dexlechem GMBH, Berlin (DE)

(72) Inventors: Maurizio Benaglia, Cadorago (IT); Martina Bonsignore, Momo (IT)

(73) Assignee: DEXLECHEM GMBH, Berlin (DE)

( * ) Notice: Subject to any disclaimer, the term of this patent is extended or adjusted under 35 U.S.C. 154(b) by 0 days.

(21) Appl. No.: 14/426,221

(22) PCT Filed: Sep. 5, 2013

(86) PCT No.: PCT/EP2013/068371
§ 371 (c)(1),
(2) Date: Mar. 5, 2015

(87) PCT Pub. No.: WO2014/037444
PCT Pub. Date: Mar. 13, 2014

(65) Prior Publication Data
US 2015/0232412 A1 Aug. 20, 2015

(30) Foreign Application Priority Data

Sep. 6, 2012 (IT) .............. MI2012A1489

(51) Int. Cl.
*C07C 29/32* (2006.01)
*C07C 209/32* (2006.01)
*C07C 213/02* (2006.01)
*C07C 231/12* (2006.01)
*C07C 221/00* (2006.01)
*C07C 227/04* (2006.01)
*C07B 43/04* (2006.01)

(52) U.S. Cl.
CPC ............. *C07C 209/325* (2013.01); *C07B 43/04* (2013.01); *C07C 213/02* (2013.01); *C07C 221/00* (2013.01); *C07C 227/04* (2013.01); *C07C 231/12* (2013.01)

(58) Field of Classification Search
None
See application file for complete search history.

(56) References Cited

PUBLICATIONS

Organic Chemistry, 2nd Edition, Seyhan Ege, Copyright C 1989 by D. C. Heath and Company, pp. 902-906.*
Guizzetti et al., Eur. J. Org. Chem. 2010, 5529-5541.*
Jones et al., Org. Biomol. Chem. 2012, 10, 2189-2200.*
Jones et al, "Trichlorosilane mediated asymmetric reductions of the C N bond," Org. Biomol. Chem. 2012, 10, 2189-2200.

\* cited by examiner

*Primary Examiner* — Karl J Puttlitz
(74) *Attorney, Agent, or Firm* — JMB Davis Ben-David

(57) ABSTRACT

Disclosed is a novel process for the reduction of nitro groups to amino derivatives, based on the use of trichlorosilane and an organic base, which is efficient from the chemical standpoint and of wide general applicability.

13 Claims, No Drawings

PROCESS FOR THE REDUCTION OF NITRO DERIVATIVES TO AMINES

CROSS-REFERENCE TO RELATED APPLICATIONS

This is the U.S. National Stage of International Application No. PCT/EP2013/068371, filed Sep. 5, 2013, which was published in English under PCT Article 21(2), which in turn claims the benefit of Italian Patent Application No. MI2012A001489, filed Sep. 6, 2012.

The invention relates to a process for the reduction of nitro groups to give amino derivatives, based on the use of trichlorosilane and an organic base, which is useful in the synthesis of various classes of compounds of interest in the pharmaceutical and agrifood industries and fine chemistry in general.

BACKGROUND TO THE INVENTION

Nitro derivatives are important starting products in organic synthesis, in which they are generally used as precursors of amino derivatives. Many aromatic nitro derivatives are commercially available or easily obtainable by nitration of suitable aromatic precursors. Aliphatic nitro derivatives are easily accessible by Michael or Henry reactions.

The reduction of nitro derivatives to amines is typically carried out by catalytic hydrogenation (Chem. Rev. 1996, 96, 2035-2052) or by various other processes, such as sodium borohydride in the presence of a catalyst (Catal. Lett. 2008, 123, 264-268), or hydrazine activated with a suitable catalyst (Adv. Synth. Catal. 2007), metals such as zinc or tin (Tetrahedron Lett. 2003, 44, 7783-7787.C), and also processes that use samarium iodide (J. Org. Chem. 2001, 66, 919-924) and complexes of molybdenum and palladium (Org. Lett. 2005, 7, 5087-5090), to name but a few.

Known catalytic systems suffer from various problems. For example, in the case of organometallic catalysts, the use of precious metals is often required, so they primarily involve a cost problem; moreover, any problems of contamination of the products with metal species and problems of disposal and suitable treatment of wastewater must be considered, as they represent serious obstacles to the use of these catalytic systems, for example in the preparation of organic compounds of potential pharmaceutical interest. In addition, it should be borne in mind that nearly all catalytic systems involve hydrogenation as the reduction process, and consequently require specific equipment.

Alternative processes are based on the use of tin salts, the toxicity of which obviously involves serious problems relating to the wastewater disposal processes and potential pollution of the reaction products.

In the case of the known catalysts, their synthesis is often not immediate and requires a synthesis sequence that can include a number of steps, which means that these molecules are neither cheap nor readily available.

In any event, all the existing processes suffer from a lack of general applicability and chemoselectivity problems towards the functional groups present in the substrate.

There is consequently great interest in identifying new processes of reducing nitro derivatives to amines, in particular for the development of new sustainable methodologies (U. Sharma, P. K. Verma, N. K. V. Kumar, M. Bala, B. Singh, Chem. Eur. J. 2011, 17, 5903) which are also economical; in this context, attention is mainly focusing on reduction processes alternative to hydrogenation, with non-toxic reagents, low environmental impact and no metals, especially by companies interested in synthesising organic molecules, including complex ones, which may be chiral or non-chiral, but are characterised by the presence of a plurality of functional groups, whose handling certainly requires the use of highly chemoselective methodologies.

Silyl hydrides (silanes) are compounds with low toxicity and limited costs that contain a silicon-hydrogen bond. Silane derivatives have been used for the reduction of nitroarenes in reactions that proceed in an incomplete way, with low yields (Zh. Obshch. Khim, 1972, 42, 176-180; Dokl. Akad. Nauk., 1970, 195, 352-355). Triethylsilane combined with the Wilkinson catalyst ($RhCl(PPh_3)_3$) has been used for the reduction of aromatic nitro derivatives to aniline (Synth. Comm. 1996, 26, 973-980), while in situ generation of molecular hydrogen by adding triethylsilane to palladium on carbon generates the reduction of nitro groups under neutral conditions (J. Org. Chem., 2007, 72, 6599-6601). Aliphatic nitro derivatives are reduced to the corresponding hydroxylamines with triethylsilane in the presence of $Pd(OAc)_2$ (Org. Lett., 2005, 7, 5087-5090).

Trichlorosilane is a very low-cost reagent which is widely used as a reducing agent for other substrates (M. Benaglia, S. Guizzetti, L. Pignataro, Coord. Chem. Rev. 2008, 252, 492). The use of this reagent in the presence of Lewis bases, as agent for the reduction of the double carbon-nitrogen bond, e.g. of imines and ketoimines, to give the corresponding amino compounds, has been described in the literature (S. Guizzetti, M. Benaglia, Eur. J. Org. Chem., 2010, 5529-5541). The use of trichlorosilane for the reduction of nitro derivatives is not known.

DESCRIPTION OF THE INVENTION

The purpose of the present invention is a process for the reduction to amine of a nitro group present in an aliphatic, cycloaliphatic, aromatic or heteroaromatic compound, in which said compound is reacted with trichlorosilane in the presence of a suitable additive, typically a base.

The process is extremely chemoselective, as it reduces the nitro groups without reacting with other functional groups present in the molecule, including those which can be attacked, for example, by a hydrogenation process.

The process of the present invention involves no problems of contamination of the reduction product by metal. Furthermore, at the end of the reaction, the exhausted reagent can be discharged into aqueous wastewater, converted to totally non-toxic derivatives.

DETAILED DESCRIPTION OF THE INVENTION

For the purpose of the present invention the term "aliphatic compound" means an organic compound containing straight or branched carbon chains, in which single carbon-carbon bonds (alkanes), double carbon-carbon bonds (alkenes) or triple carbon-carbon bonds (alkynes) may be present.

The term "cycloaliphatic compound" means an organic aliphatic compound as defined above, in which the carbon chains form a non-aromatic ring.

The term "aromatic compound" means an organic compound having one or more carbon rings with aromatic structure. The aromatic compounds can be monocyclic or polycyclic. Examples of aromatic compounds are benzene, naphthalene, anthracene and phenanthrene.

The term "heteroaromatic compound" means an aromatic organic compound as defined above in which one or more carbons of an aromatic ring are replaced by oxygen, sulphur or nitrogen atoms. Examples of heteroaromatic compounds are pyridine, pyrimidine, pyrazine, pyridazine, triazine, furan, thiophene, pyrrole, imidazole, pyrazole, thiazole, isothiazole, oxazole, isoxazole, triazole, tetrazole, quinoline, isoquinoline, indole, benzofuran, benzothiophene, benzothiazole, indazole, benzoimidazole, carbazole, 1,2,4-thiadiazole and the like.

A trichlorosilane to nitro group molar ratio ranging from 1 to 5, preferably 3.5, is used in the process of the present invention.

The reaction is carried out in the presence of an organic base, typically secondary and tertiary organic amines such as triethylamine (TEA), N,N-diethylisopropylamine, N,N-diisopropylethylamine (DIPEA), diethylamine, tripropylamine and trioctylamine. A base to nitro group molar ratio ranging from 1 to 10, preferably from 3 to 5, is typically used. Diisopropylethylamine is preferably used for the reduction of aliphatic nitro derivatives, whereas triethylamine or diisopropylethylamine are preferably used for the reduction of aromatic or heteroaromatic nitro derivatives.

The process is usually carried out in the presence of an organic solvent, which can be chlorinated, aromatic or polar, or mixtures thereof, preferably dichloromethane, chloroform, acetonitrile, propionitrile, toluene, benzene, chlorobenzene and tetrahydrofuran. Acetonitrile is preferred.

The reaction is effected at a temperature from −50° C. to 35° C., preferably from 0° C. to 15° C., and is usually complete in a time ranging from 2 to 48 hours, typically 15 hours.

The process of the invention provides achiral and chiral amino compounds in high yields. The process has high chemoselectivity which allows the nitro groups to be reduced, even in the presence of many other potentially reducible functionalities which, however, are left unchanged. In one embodiment of the invention, the nitro derivative that undergoes the reduction to amine therefore also contains at least one functional group selected from the group consisting of a double or triple carbon-carbon bond; a carbonyl group, preferably acetyl or formyl; halogen; C1-C4 hydroxyalkyl, preferably hydroxymethyl; allyl ether; C7-C18 aryl alkyl ether, preferably benzyl ether; C1-C4 acylamino, preferably acetylamino; nitrile; carboxyl; carboxyl or thio-carboxyl ester selected from C1-C4 alkyl ester, C6-C14 aryl ester or C7-C18 aryl alkyl ester, preferably benzyl ester; or the nitro derivative can contain another nitro group which is not necessarily reduced to amine, depending on the reaction conditions.

The process of the invention can be used as one step of a multi-step process, in which the amino derivative obtained is used in a subsequent synthetic transformation, optionally without being isolated.

The process of the invention is effected under very economical reaction conditions. Unlike the vast majority of organometallic systems, which almost always require more drastic conditions and heating of the reaction mixture, the mild reaction conditions and extreme operational simplicity of the process of the invention make it attractive for industrial use.

The processing of the reaction mixture also involves simple washing with aqueous solutions that solubilise the reducing agent and the products formed by it, leaving the amino derivative, which is substantially already pure, in organic phase, often with no need for further purification.

Finally, a further advantage of the process of the present invention is the non-toxicity of trichlorosilane and its reaction products.

The invention will now be illustrated by the following examples.

Example 1

General Procedure for the Reduction of Aliphatic Nitro Derivatives

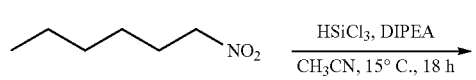

-continued

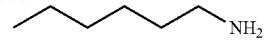

DIPEA (5 mmol/eq) was added to a solution of 1-nitro-n-hexane (1 mmol/eq) in acetonitrile at 15° C., maintained under stirring. Freshly distilled trichlorosilane (3.5 mmol/eq) was then added dropwise with a syringe. After leaving under stirring for 18 hours at 15° C., the reaction was quenched by adding 10% NaOH, and the mixture was extracted with AcOEt. The combined organic phases were dried on $Na_2SO_4$, filtered and concentrated under vacuum to give the corresponding amine in a quantitative yield.

Example 2

The same procedure as described in Example 1 was used to reduce functionalised aliphatic substrates, such as 2-nitropropan-1-ol and 3-nitropropanoic acid, obtaining the corresponding amines in a quantitative yield, as illustrated in Schemes 1 and 2 respectively.

Scheme 1

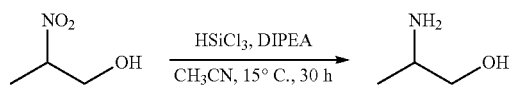

Scheme 2

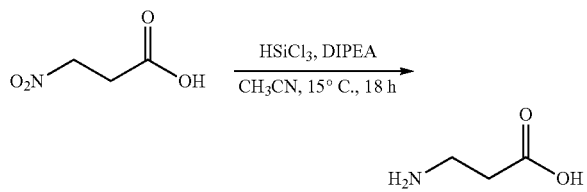

Example 3

General Procedure for the Reduction of Aromatic Nitro Derivatives

DIPEA (5 mmol/eq) was added to a solution of the aromatic nitro derivative (1 mmol/eq) in acetonitrile at 15° C., maintained under stirring. Freshly distilled trichlorosilane (3.5 mmol/eq) was then added dropwise with a syringe. After leaving under stirring for 18 hours at 15° C., the reaction was quenched by adding a $NaHCO_3$ saturated aqueous solution, and the mixture was extracted with AcOEt. The combined organic phases were dried on $Na_2SO_4$, filtered and concentrated under vacuum to give the corresponding amine.

By applying the procedure described above to different aromatic nitro substrates and using triethylamine (TEA) as base (Scheme 3), the corresponding amines were obtained with the yields reported in the Table.

Scheme 3

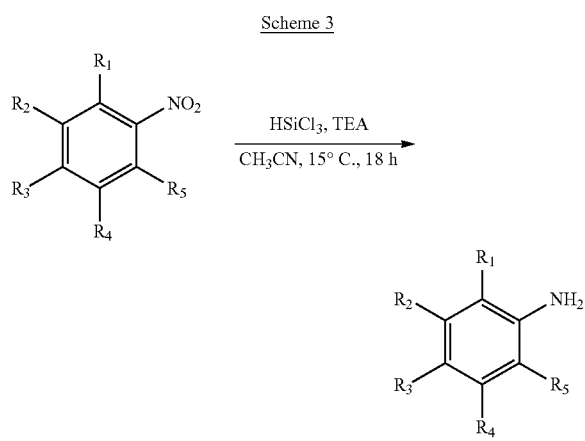

TABLE

| Compound | $R_1$ | $R_2$ | $R_3$ | $R_4$ | $R_5$ | Yield (%) |
|---|---|---|---|---|---|---|
| 1 | H | H | Cl | H | H | >99 |
| 2 | H | H | $CH_2OH$ | H | H | 75 |
| 3 | H | H | O-allyl | H | H | 92 |
| 4 | O-allyl | H | H | H | H | 87 |
| 5 | H | H | OBn | H | H | >99 |
| 6 | OBn | H | H | H | H | >99 |
| 7 | H | H | NHAc | H | H | 40 |
| 8 | H | H | $COCH_3$ | H | H | 70 |
| 9 | CHO | H | H | H | H | >99 |
| 10 | H | H | COOH | H | H | 47 |
| 11 | H | H | COOEt | H | H | 77 |

The invention claimed is:

1. Process for the reduction to amine of a nitro group present in an aliphatic, cycloaliphatic, aromatic or heteroaromatic compound, wherein said compound is reacted with trichlorosilane in the presence of a base.

2. Process according to claim 1, wherein a trichlorosilane to nitro group molar ratio ranging from 1 to 5 is used.

3. Process according to claim 2, wherein the trichlorosilane to nitro group molar ratio is 3.5.

4. Process according to claim 1, wherein said base is an organic base selected from the group consisting of secondary or tertiary amines.

5. Process according to claim 4, wherein the organic base is triethylamine or diisopropylethylamine.

6. Process according to claim 4, wherein a base to nitro group molar ratio ranging from 1 to 10 is used.

7. Process according to claim 6, wherein the base to nitro group molar ratio is 5.

8. Process according to claim 1, wherein the nitro group is present in an aromatic or heteroaromatic compound and the base is triethylamine or diisopropylethylamine.

9. Process according to claim 1, wherein the nitro group is present in an aliphatic or cycloaliphatic compound and the base is diisopropylethylamine.

10. Process according to claim 1, wherein the nitro group is present in an alkene.

11. Process according to claim 1, wherein the nitro group is present in a compound which contains at least one functional group selected from the group consisting of a double or triple carbon-carbon bond; a carbonyl group; halogen; C1-C4 hydroxyalkyl; allyl ether; C7-C18 arylalkyl ether; C1-C4 acylamino; nitrile; carboxyl; a carboxylic or thio-carboxylic ester selected from the group consisting of C1-C4 alkyl ester, C6-C14 aryl ester or C7-C18 arylalkyl ester.

12. Process according to claim 11, wherein the functional group is selected from the group consisting of acetyl, formyl, hydroxymethyl, benzyl ether, acetylamino, benzyl ester.

13. Process according to claim 1, wherein at the end of the reduction of the nitro group to amine, the compound is not isolated.

* * * * *